US012565469B2

(12) United States Patent
Zanthoff et al.

(10) Patent No.: US 12,565,469 B2
(45) Date of Patent: Mar. 3, 2026

(54) METHOD FOR RING HYDROGENATION OF DIALKYL TEREPHTHALATES WITH LOW BY-PRODUCT FORMATION

(71) Applicant: Evonik Oxeno GmbH & Co. KG, Marl (DE)

(72) Inventors: Horst-Werner Zanthoff, Muelheim a.d. Ruhr (DE); Julia Bauer, Haltern am See (DE); Michael Grass, Haltern am See (DE); Thomas Schneider, Schermbeck (DE)

(73) Assignee: Evonik Oxeno GmbH & Co. KG, Marl (DE)

( * ) Notice: Subject to any disclaimer, the term of this patent is extended or adjusted under 35 U.S.C. 154(b) by 802 days.

(21) Appl. No.: 17/931,559

(22) Filed: Sep. 13, 2022

(65) Prior Publication Data

US 2023/0092962 A1      Mar. 23, 2023

(30) Foreign Application Priority Data

Sep. 14, 2021      (EP) ..................................... 21196659

(51) Int. Cl.
| | |
|---|---|
| *C07C 67/303* | (2006.01) |
| *B01J 21/04* | (2006.01) |
| *B01J 21/06* | (2006.01) |
| *B01J 23/46* | (2006.01) |

(52) U.S. Cl.
CPC ............. *C07C 67/303* (2013.01); *B01J 21/04* (2013.01); *B01J 21/06* (2013.01); *B01J 23/462* (2013.01)

(58) Field of Classification Search
CPC ........ C07C 67/303; C07C 69/75; B01J 21/04; B01J 21/06; B01J 23/462
See application file for complete search history.

(56) References Cited

U.S. PATENT DOCUMENTS

| | | | |
|---|---|---|---|
| 2006/0161017 A1* | 7/2006 | Grass et al. ............ | C07C 61/09 562/509 |
| 2006/0167151 A1 | 7/2006 | Grass et al. | |
| 2021/0032189 A1 | 2/2021 | Poplow | |
| 2022/0380294 A1 | 12/2022 | Gubisch et al. | |

OTHER PUBLICATIONS

U.S. Appl. No. 17/804,015, filed May 25, 2022, 2022/0380294, Gubisch et al.
European Search Report dated Feb. 24, 2022, in European Application No. 21196659.3, 5 pages.

* cited by examiner

*Primary Examiner* — Amy C Bonaparte
*Assistant Examiner* — Derek Rhoades
(74) *Attorney, Agent, or Firm* — Grüneberg Global IP, PLLC

(57) ABSTRACT

A process for ring hydrogenation of dialkyl terephthalates having $C_3$- to $C_{16}$-alkyl groups can be performed in a hydrogenation unit composed of two reaction units in series. In the process, a suitable process parameter in relation to the first reaction unit is adjusted so that a certain reaction conversion is achieved.

20 Claims, No Drawings

METHOD FOR RING HYDROGENATION OF DIALKYL TEREPHTHALATES WITH LOW BY-PRODUCT FORMATION

CROSS-REFERENCE TO RELATED APPLICATIONS

This application claims priority to European Application No. 21196859.3, filed on Sep. 14, 2021, the content of which is hereby incorporated by reference in its entirety.

BACKGROUND OF THE INVENTION

Field of the Invention

The present invention relates to a process for the ring hydrogenation of dialkyl terephthalates having $C_3$- to $C_{16}$-alkyl groups in a hydrogenation unit composed of two reaction units in series. In the process according to the invention, a suitable process parameter in relation to the first reaction unit is controlled so that a certain reaction conversion is achieved.

DESCRIPTION OF RELATED ART

Plasticizers are used in many industrial fields in order to make plastics such as polyvinyl chloride (PVC) softer and more elastic. Phthalates, that is to say the diesters of (ortho-) phthalic acid, have for many years been the dominant plasticizer class. However, in recent years there has also been an increase in the significance of the alkyl esters of cyclohexanedicarboxylic acids, not least on account of the debate around possible health concerns of phthalate-based plasticizers. The primary role is here played by dialkyl 1,2-cyclohexanedicarboxylates, and more recently too by dialkyl 1,4-cyclohexanedicarboxylates.

Dialkyl 1,2- and 1,4-cydohexanedicarboxylates can be prepared by hydrogenation (hereinafter used synonymously with the term ring hydrogenation) of the aromatic ring of the corresponding phthalates or terephthalates. Corresponding ring hydrogenations are nowadays already used on an industrial scale for phthalates, i.e. dialkyl phthalates, for example in the conversion of DINP (diisononyl phthalate) to DINCH (1,2-diisononyl cyclohexanedicarboxylate. With regard to the hydrogenation of terephthalates, i.e. dialkyl terephthalates, it is assumed that such processes are economically less interesting, since the reaction of dialkyl terephthalates proceeds more slowly and more by-products are formed than in the case of ring hydrogenation of dialkyl phthalates.

SUMMARY OF THE INVENTION

The object therefore was therefore that of providing an improved method for ring hydrogenation of dialkyl terephthalates which may be operated economically also compared to the ring hydrogenation of dialkyl phthalates. The object of the present invention was therefore that of providing a method for ring hydrogenation of dialkyl terephthalates in a hydrogenation unit which enables a more efficient production of the corresponding esters.

The object was achieved by the process described below for ring hydrogenation of dialkyl terephthalates having $C_3$- to $C_{16}$-alkyl groups. Preferred configurations of this process are also specified below.

The invention also includes the following embodiments:

1. Process for ring hydrogenation of dialkyl terephthalates having $C_3$- to $C_{16}$-alkyl groups, preferably dialkyl terephthalates having $C_4$- to $C_{11}$-alkyl groups, to give 1,4-cyclohexanedicarboxylic esters having the corresponding alkyl groups, in a hydrogenation unit consisting or two reaction units connected in series, which consist of one reactor or two or more parallel reactors, of which the reactor(s) in the second reaction unit are operated in a straight pass, wherein a heterogeneous hydrogenation catalyst is present in the reactors of each of the two reaction units of the hydrogenation unit and wherein the process is characterized in that the aromatic carboxylic ester used as feed to the reactors of the reaction units is brought into contact with a hydrogen-containing gas, wherein the reaction conversion in the first reaction unit is monitored, and wherein at least one parameter in relation to the first reaction unit, selected from the group consisting of the amount of feed supplied to the first reaction unit (total amount or fresh reed and recycle), the amount of dialkyl terephthalate to be hydrogenated, the reactor temperature in the reactor(s) of the first reaction unit, the temperature increase, the circulation volume flow, the feed/recycle ratio, the ratio of hydrogen to aromatic carboxylic ester, the reactor pressure, the feed composition, the amount of catalyst, the catalyst composition, if cooling is present, the amount of coolant circulated or the amount of product in the discharge of the first reaction unit and a combination thereof, is controlled such that a reaction conversion in the range of 85 to 93%, preferably 88 to 92%, is achieved.

2. Process according to embodiment 1, wherein a reactor is present in the first reaction unit, which is operated in a closed loop.

3. Process according to embodiments 1 and 2, wherein the amount of by-products in the ring hydrogenation process product after the hydrogenation unit is less than 1.3% by weight, preferably less than 1.2% by weight.

4. Process according to any of the preceding embodiments, wherein the total conversion in the process, based on the total hydrogenation unit, is greater than or equal to 99.7%, preferably greater than or equal to 99.8%.

5. Process according to any of the preceding embodiments, wherein the dialkyl terephthalate used in the ring hydrogenation is a dialkyl terephthalate having $C_4$- to $C_{10}$-alkyl groups, preferably a dialkyl terephthalate having $C_5$- to $C_9$-alkyl groups, particularly preferably a dialkyl terephthalate having $C_8$- or $C_9$-alkyl groups.

6. Process according to embodiment 5, wherein the dialkyl terephthalate used in the ring hydrogenation is prepared by transesterification of dimethyl terephthalate with an alcohol having 4 to 10 carbon atoms or by esterification of terephthalic acid with an alcohol having 4 to 10 carbon atoms.

7. Process according to embodiment 5, wherein the dialkyl terephthalate used in the ring hydrogenation is diethylhexyl terephthalate or diisononyl terephthalate.

8. Process according to any of the preceding embodiments, wherein the heterogeneous hydrogenation catalyst used in the ring hydrogenation in the reactors of the two reactor units of the hydrogenation unit comprises a transition metal on a support material.

9. Process according to embodiment 8, wherein the transition metal is a metal from Group 8 of the Periodic Table of the Elements (iron group), preferably ruthenium.

10. Process according to embodiment 8 or 9, wherein the support material is selected from the group consisting of activated carbon, silicon carbide, aluminium oxide, silicon dioxide, aluminosilicate, zeolites, titanium dioxide, zirconium dioxide, magnesium oxide, zinc oxide or mixtures thereof.

11. Process according to embodiment 10, wherein the support material is titanium dioxide or aluminium oxide.

12. Process according to any of embodiments 8 to 11, wherein the transition metal content in the heterogeneous hydrogenation catalyst is in the range from 0.1% to 10% by weight, preferably particularly in the range from 0.2% to 5% by weight, particularly in the range from 0.5% to 3% by weight.

13. Process according to any of embodiments 8 to 12, wherein the hydrogenation catalysts in the at least two reactors of the hydrogenation unit have the same composition.

14. Process according to any of the preceding embodiments, wherein the hydrogenation temperature in the ring hydrogenation is in the range from 50 to 250° C.

15. Process according to any of the preceding embodiments, wherein the ring hydrogenation is carried out in a pressure range of 3 to 300 bar.

DETAILED DESCRIPTION OF THE INVENTION

Accordingly, the process according to the invention is a process for ring hydrogenation of dialkyl terephthalates having $C_3$- to $C_{16}$-alkyl groups, preferably dialkyl terephthalates having $C_4$- to $C_{11}$-alkyl groups, to give 1,4-cyclo-hexanedicarboxylic esters having the corresponding alkyl groups, in a hydrogenation unit consisting of two reaction units connected in series, which consist of one reactor or two or more parallel reactors, which are operated in recirculating mode or in straight-pass mode, of which the reactor(s) in the second reaction unit are operated in straight-pass mode, wherein a heterogeneous hydrogenation catalyst is present in the reactors of each of the two reaction units of the hydrogenation unit and wherein the process is distinguished in that the aromatic carboxylic ester used as feed to the reactors of the reaction units is brought into contact with a hydrogen-containing gas, wherein the reaction conversion in the first reaction unit is monitored, and wherein at least one parameter in relation to the first reaction unit, selected from the group consisting of the amount of feed supplied to the first reaction unit (total amount of fresh feed and recycle), the amount of dialkyl terephthalate to be hydrogenated, the reactor temperature in the reactor(s) of the first reaction unit, the temperature increase, the circulation volume flow, the feed/recycle ratio, the ratio of hydrogen to aromatic carboxylic ester, the reactor pressure, the feed composition (for example inhibition of the reaction by adding, for example, substances which specifically reduce the activity of the catalyst), the amount of catalyst, the catalyst composition, if cooling is present, the amount of coolant circulated or the amount or product in the discharge of the first reaction unit and a combination thereof, is controlled such that a reaction conversion in the range of 85 to 93%, preferably 88 to 92%, is achieved.

Surprisingly, it has been found that limiting the reaction conversion in the first reaction unit results in the fact that the amount of by-products and/or the amount of reactant in the final hydrogenation product (after passing through the second reaction unit) can be reduced. The reaction product obtained is thus purer and requires less-complex purification or is directly available in the required specification, so that it can be sold or used further without additional purification effort.

According to the invention, the hydrogenation unit consists of two reaction units connected in series, which each consist of one reactor or two or more reactors in parallel. In the second reaction unit, the reactor(s) are operated in straight pass. The reactor(s) in the first reaction unit may be operated in various ways. However, it is preferable when a reactor is present in the first reaction unit, that this is operated in a closed loop. The reaction conversion is then adjusted with respect to the inlet feed and inlet to the second reactor unit.

The parameter which is controlled to limit the conversion in the parallel reactor(s) of the first reaction unit, in the context of the present invention, is preferably selected from the group consisting of the amount of feed supplied to the at least one loop reactor (total amount of fresh feed and recycle), the amount of dialkyl terephthalate to be hydrogenated, the reactor temperature in the at least one loop reactor, the temperature increase (i.e. difference between the temperature at the reactor inlet and the temperature at the reactor outlet), the circulation volume flow, the feed/recycle ratio, the reactor pressure, if cooling is present, the amount of coolant circulated, the amount of product in the discharge of the first reaction unit, and a combination thereof. Appropriate measures to regulate these parameters are familiar to those skilled in the art. In a particularly preferred embodiment, the parameter which is controlled for limiting the conversion in the parallel reactor(s) of the first reaction unit, in the context of the present invention, is preferably selected from the group consisting of the amount of feed supplied to the at least one loop reactor (total amount of fresh feed and recycle), the amount of dialkyl terephthalate to be hydrogenated, the feed/recycle ratio and a combination thereof. This is particularly advantageous since the reaction throughput can be significantly increased, which means that more product can be formed in a shorter time with a small amount of by-products.

With respect to adjusting the amount of product in the discharge of the first reaction unit, as a way of adjusting the reaction conversion: limiting the reaction conversion can also be produced purely by calculation by routing a portion of the feed used around the first reaction unit, i.e. by not passing through the reactor(s) of the reaction unit and not being hydrogenated. The portion of the feed routed around the first reaction unit is then mixed with the reaction discharge of the first reaction unit, thereby controlling the amount of product in the discharge of the first reaction unit, and conducted to the second reaction unit with the reactor(s) operated in straight pass. The stream supplied to the second reaction unit then has a composition which corresponds to the composition of a reaction discharge from the first reaction unit in which a reaction conversion in the range of 85 to 93%, preferably 88 or 92%, has been attained. This can be very simply controlled by the amount of feed routed around the first reaction unit. In this embodiment, the desired conversion in the first reaction unit is thus only contrived. The true reaction conversion in the first reaction unit can be (significantly) higher and is artificially lowered by addition of feed.

The process according to the invention could in principle be carried out batchwise or continuously. According to the invention, it is preferably a continuous process. Despite limiting the reaction conversion in the first reaction unit, the process according to the invention achieves an overall conversion based on the entire hydrogenation unit of greater than or equal to 99.7%, preferably greater than or equal to 99.8%. The amount of by-products in the ring hydrogenation process product after the hydrogenation unit is preferably less than 1.3% by weight, particularly preferably less than 1.2% by weight.

According to the invention, dialkyl terephthalates having $C_3$- to $C_{16}$-alkyl groups are used in the ring hydrogenation. The choice of the length of the alkyl groups is less critical and should not pose any problems to those skilled in the art. However, it is preferred that the two alkyl groups have the same chain length. The dialkyl terephthalate used is preferably dialkyl terephthalate having $C_4$- to $C_{11}$-alkyl groups, further preferably a dialkyl terephthalate having $C_4$- to $C_{10}$-alkyl groups, further preferably a dialkyl terephthalate having $C_5$- to $C_9$-alkyl groups, particularly preferably a dialkyl terephthalate having $C_8$- or $C_9$-alkyl groups. The dialkyl terephthalate used is especially preferably diethylhexyl terephthalate or diisononyl terephthalate.

The dialkyl terephthalate used in the ring hydrogenation can be prepared by transesterification of esters of terephthalic acid, for example dimethyl terephthalate with an appropriate alcohol, or by esterification of terephthalic acid with an appropriate alcohol. The chain length of the alcohol used corresponds to the chain length in the ester formed.

In accordance with the invention, heterogeneous hydrogenation catalysts are used in the process according to the invention for ring hydrogenation of dialkyl terephthalates or aromatic carboxylic esters in general. These may be catalysts comprising a support material, or unsupported catalysts (without support material), for example Raney Ni. The heterogeneous hydrogenation catalyst used in the ring hydrogenation in the at least two reactors of the hydrogenation unit comprises at least one transition metal on a support material or consists of at least one transition metal on a support material. Suitable catalysts are also familiar to the person skilled in the art and can be found, for example, in WO 03/103830 A1.

The transition metal of the heterogeneous hydrogenation catalyst is preferably a metal selected from Group 8 of the Periodic Table of the Elements (iron group), preferably from the group consisting of iron, ruthenium, cobalt, nickel, rhodium, platinum, palladium or mixtures thereof. Ruthenium is the transition metal for the catalyst used which is particularly preferred in the present invention. The transition metal content in the heterogeneous hydrogenation catalyst is preferably in the range from 0.1% to 10% by weight, preferably particularly in the range from 0.2% to 5% by weight, especially in the range from 0.5% to 3% by weight. If ruthenium is used as transition metal, the ruthenium content, calculated as the metal, is preferably in the range from 0.1% to 10% by weight, especially in the range from 0.2% to 5% by weight, very particularly in the range between 0.5% and 3% by weight.

The support material on which the transition metal of the heterogeneous hydrogenation catalyst is present is preferably selected from the group consisting of activated carbon, silicon carbide, aluminium oxide, silicon dioxide, aluminosilicate, zeolites, titanium dioxide, zirconium dioxide, magnesium oxide, zinc oxide or mixtures thereof. Preferred support materials are aluminium oxide, silicon dioxide, titanium dioxide and mixtures thereof, particular preference being given to titanium dioxide and aluminium oxide. In addition, these support materials may comprise alkali metal, alkaline earth metal and/or sulfur components.

The heterogeneous hydrogenation catalysts in the reactors of both reaction units may have the same or a different composition of transition metal and support material. The at least two heterogeneous hydrogenation catalysts preferably have the same composition, i.e. they comprise the same transition metal and the same support material, wherein the transition metal content, preferably the ruthenium content, may be different.

The ring hydrogenation is according to the invention preferably carried out in the liquid phase. Ring hydrogenation can be carried out with homogeneous hydrogenation catalysts or heterogeneous hydrogenation catalysts arranged in suspended or lumpy form in a fixed bed. In the process according to the invention, preference is given to continuous ring hydrogenation over a heterogeneous catalyst in a fixed bed, in which the reaction mixture is mainly in the liquid state under the reaction conditions. Preference is given to operating the reactor(s) with a liquid/gas mixed phase, for example as trickle bed reactor(s) that may be completely or partly flooded.

Various process variants may be chosen for the ring hydrogenation. It may be carried out adiabatically or polytropically, in one or more stages. In the latter case, all reactors, appropriately tubular reactors, may be operated adiabatically or polytropically, or else one or more adiabatically and the others polytropically.

The ring hydrogenation according to the invention may be carried out in cocurrent in the liquid/gas mixed phase or in the liquid phase in triphasic reactors, with the hydrogenation gas introduced into the liquid reactant/product stream in a manner known per se. In the interests of a uniform liquid distribution, of improved removal of heat of reaction and of a high space-time yield, the reactors are preferably operated with high liquid loads of 15 to 120, especially of 25 to 80, $m^3$ per $m^2$ of cross section of the empty reactor and per hour. When a reactor is operated in straight pass, the specific liquid hourly space velocity (LHSV) may assume values between 0.1 and 10 $h^{-1}$.

In a preferred embodiment, the process for ring hydrogenation may be carried out in the absence or preferably in the presence of a solvent. The solvent used may be all liquids that form a homogeneous solution with the reactant and product, are inert under hydrogenation conditions and can be easily removed from the product.

For example, it is possible to use the following substances as solvent: straight-chain or cyclic ethers such as tetrahydrofuran or dioxane and also aliphatic alcohols in which the alkyl radical has 1 to 13 carbon atoms. Alcohols or alcohol mixtures usable with preference are, for example, isopropanol, n-butanol, isobutanol, n-pentanol, 2-ethylhexanol, nonanols, technical-grade nonanol mixtures, decanol, technical-grade decanol mixtures, tridecanols.

When alcohols are used as solvent, it may be appropriate to use that alcohol or that alcohol mixture that would form in hydrolysis of the product. This rules out by-product formation through transesterification. A further preferred solvent is the hydrogenation product, here the ring-hydrogenated dialkyl terephthalates themselves.

The ring hydrogenation can be conducted within a pressure range from 3 to 300 bar, preferably 20 to 200 bar. The hydrogenation temperatures are preferably in the range from 50° C. to 250° C. especially in the range from 60° C. to 200° C.

Hydrogenation gases used may be any desired hydrogen-containing gas mixtures that do not contain harmful amounts of catalyst poisons, for example carbon monoxide or hydrogen sulfide. In addition to hydrogen, for example $CO_2$, nitrogen or methane may also be present in the hydrogenation gas. Preference is given to using hydrogen at a purity of greater than 95%, especially greater than 98%.

The invention is elucidated hereinafter by examples. These examples disclose exemplary embodiments and should not be regarded as limiting.

EXAMPLE

Hydrogenation experiments with diisononyl phthalate (DINP) and diisononyl terephthalate (DINT) were conducted in a hydrogenation unit, which consisted of a loop reactor and a reactor operated in straight pass, as follows:

The ring hydrogenation of DINT or DINP was conducted in a tubular reactor in circulation operation mode connected with a second tubular reactor in straight pass mode. There was cocurrent flow of liquid phase (DINT or DINP and hydrogenation product) and gas phase (hydrogen) in the trickle bed of the tubular reactors. A commercially available ruthenium catalyst (Specialyst® 102: 1% Ru on a $TiO_2$ support, Evonik Operations GmbH) was used as hydrogenation catalyst in both reactors. This was used in tubular reactor in circulating operation having an internal diameter of 40 mm and a length of 479 mm and in the second reactor having an internal diameter of 20 mm and a length of 1076 mm. The feed rate of DINT or DINP used in the ring hydrogenation was varied depending on the experiment between ca. 180-800 g/h; the cycle stream was invariably 80 l/h. The feed rate was altered during the reaction in order thereby to influence the reaction conversion. The hydrogen level was under closed-loop control by means of a constant offgas mode with an offgas flow rate of 0.5 l/h. The experiments were each carried out at a system pressure of 100 bar and a tubular reactor temperature of 105° C. In the loop reactor and 110° C. in the second reactor. The discharge from the hydrogenation unit was analyzed for the presence and the amount of by-products by means of gas chromatography (GC). The results are shown in Table 1 below:

| Reactant | Temperature/ ° C. | Feed rate/ g/h | Conversion in the loop reactor/% | Total conversion (after last reactor)/% | Amount of by-products after last reactor/% by weight |
|---|---|---|---|---|---|
| DINT | 105 | 246 | 95.1 | >99.8 | 1.49 |
| DINT | 105 | 397 | 91.0 | >99.8 | 1.11 |
| DINT | 105 | 429 | 90.0 | >99.8 | 1.02 |
| DINP | 105 | 427 | 94.9 | >99.8 | 0.49 |
| DINP | 105 | 792 | 90.1 | >99.8 | 0.43 |

In the ring hydrogenation of the terephthalate, it can be seen that by limiting the conversion in the first reactor, the amount of by-products after the last reactor can be significantly reduced. Conversely, in the case of the corresponding phthalate, this change is minimal. Limiting the conversion of the terephthalate has the further advantage here that the feed rate can be significantly increased. Therefore, more ring-hydrogenated product at higher purity can be produced and thus the economic efficiency of the process increased.

The invention claimed is:

1. A process for ring hydrogenation of a dialkyl terephthalate having $C_3$- to $C_{16}$-alkyl groups, to give a 1,4-cyclohexanedicarboxylic ester having corresponding alkyl groups, the process comprising:

contacting the dialkyl terephthalate with a hydrogen-containing gas, in a hydrogenation unit consisting of a first reaction unit and a second reaction unit connected in series, wherein the first reaction unit and the second reaction unit each consist of one reactor or two or more parallel reactors, wherein reactor(s) of the second reaction unit are operated in a straight pass, wherein reactor(s) of the first reaction unit and the reactor(s) of the second reaction unit each independently comprise a heterogeneous hydrogenation catalyst, wherein the dialkyl terephthalate is used as feed to the reactor(s) of the first reaction unit and the reactor(s) of the second reaction unit, wherein a reaction conversion in the first reaction unit is monitored, and wherein at least one parameter in relation to the first reaction unit, selected from the group consisting of an amount of feed supplied to the first reaction unit (total amount of fresh feed and recycle), an amount of dialkyl terephthalate to be hydrogenated, a reactor temperature in the reactor(s) of the first reaction unit, a temperature increase, a circulation volume flow, a feed/recycle ratio, a ratio of hydrogen to the dialkyl terephthalate, a reactor pressure, a feed composition, an amount of the heterogeneous hydrogenation catalyst, a catalyst composition, if cooling is present, an amount of coolant circulated or an amount of product in a discharge of the first reaction unit, and a combination thereof, is controlled such that a reaction conversion in the range of 85 to 93% is achieved.

2. The process according to claim 1, wherein a reactor present in the first reaction unit is operated in a closed loop.

3. The process according to claim 1, wherein an amount of by-products in a ring hydrogenation process product after the hydrogenation unit is less than 1.3% by weight.

4. The process according to claim 1, wherein a total conversion in the process, based on the hydrogenation unit, is greater than or equal to 99.7%.

5. The process according to claim 1, wherein the dialkyl terephthalate is a dialkyl terephthalate having $C_4$- to $C_{10}$-alkyl groups.

6. The process according to claim 5, wherein the dialkyl terephthalate is prepared by transesterification of dimethyl terephthalate with an alcohol having 4 to 10 carbon atoms, or by esterification of terephthalic acid with an alcohol having 4 to 10 carbon atoms.

7. The process according to claim 5, wherein the dialkyl terephthalate is diethylhexyl terephthalate or diisononyl terephthalate.

8. The process according to claim 1, wherein the heterogeneous hydrogenation catalyst of the reactor(s) of the first reaction unit and of the reactor(s) of the second reaction unit each comprise a transition metal on a support material.

9. The process according to claim 8, wherein the transition metal is a metal from Group 8 of the Periodic Table of the Elements.

10. The process according to claim 8, wherein the support material is selected from the group consisting of activated carbon, silicon carbide, aluminium oxide, silicon dioxide, aluminosilicate, a zeolite, titanium dioxide, zirconium dioxide, magnesium oxide, zinc oxide, and a mixture thereof.

11. The process according to claim 10, wherein the support material is titanium dioxide or aluminium oxide.

12. The process according to claim 8, wherein a transition metal content in the heterogeneous hydrogenation catalyst is in the range from 0.1% to 10% by weight.

13. The process according to claim 8, wherein the heterogenous hydrogenation catalyst of both the reactor(s) of the first reaction unit and the reactor(s) of the second reaction unit have the same composition.

14. The process according to claim 1, wherein a hydrogenation temperature in the ring hydrogenation is in the range from 50 to 250° C.

15. The process according to claim 1, wherein the ring hydrogenation is carried out in a pressure range of 3 to 300 bar.

16. The process according to claim 1, wherein the reaction conversion of the first reaction unit is in a range of 88 to 92%.

17. The process according to claim 5, wherein the dialkyl terephthalate is a dialkyl terephthalate having $C_5$- to $C_9$-alkyl groups.

18. The process according to claim 5, wherein the dialkyl terephthalate is a dialkyl terephthalate having $C_8$- or $C_9$-alkyl groups.

19. The process according to claim 9, wherein the transition metal is ruthenium.

20. The process according to claim 12, wherein the transition metal content in the heterogeneous hydrogenation catalyst is in a range from 0.5% to 3% by weight.

\* \* \* \* \*